United States Patent [19]
Jordan et al.

[11] Patent Number: 5,661,657
[45] Date of Patent: Aug. 26, 1997

[54] SYSTEM AND METHOD FOR PERFORMING MULTIPLE, RANDOM, ASYNCHRONOUS ELECTROSTATIC DISCHARGES

[75] Inventors: Stanley Robert Jordan, Boca Raton, Fla.; Howard Herbert Nick, Lagrangeville, N.Y.; Brock Estel Osborn, Hyde Park, N.Y.; Chang-Yu Wu, Wappingers Falls, N.Y.

[73] Assignee: International Business Machines Corporation, Armonk, N.Y.

[21] Appl. No.: 385,318

[22] Filed: Feb. 8, 1995

[51] Int. Cl.⁶ ............................................. H01T 19/00
[52] U.S. Cl. ...................... 364/481; 364/579; 324/72.5
[58] Field of Search ............................. 324/457, 754, 324/755, 452, 72, 72.5; 364/579, 580, 483, 481; 361/230, 212; 340/649, 635

[56] References Cited

U.S. PATENT DOCUMENTS

| | | | |
|---|---|---|---|
| 4,885,543 | 12/1989 | Smith | 324/452 |
| 4,961,157 | 10/1990 | Nick et al. | 364/579 |
| 5,083,117 | 1/1992 | Hoigaard | 340/649 |
| 5,132,612 | 7/1992 | Burns et al. | 324/755 |
| 5,557,195 | 9/1996 | Schrimph et al. | 324/72 |

*Primary Examiner*—Benedict V. Safourek
*Assistant Examiner*—Min Jung
*Attorney, Agent, or Firm*—Calfee, Halter & Griswold LLP

[57] ABSTRACT

A system having a computer, test control logic, an electrostatic discharge unit and a high voltage probe unit is provided for performing multiple, random, asynchronous electrostatic discharge testing of machines. The test control logic includes multiple, asynchronous, random, firing logic for controlling the states of a plurality of output lines which send control signals from the computer to the electrostatic discharge unit and the high voltage probe unit. The test control logic allows a user a preference of testing modes through an interactive input graph. The user may specify either a run time experiment or a specific probability of test coverage test.

27 Claims, 6 Drawing Sheets

SYSTEM AND METHOD FOR PERFORMING MULTIPLE, RANDOM, ASYNCHRONOUS ELECTROSTATIC DISCHARGES

FIELD OF THE INVENTION

The present invention relates generally to electrostatic discharge testing of machines and, more specifically, to a system and method for generating multiple, random, asynchronous electrostatic discharge testing of computer related machines to insure a specified level of confidence in the test result.

BACKGROUND OF THE INVENTION

Digital equipment, and computers in particular, are very sensitive to electrostatic discharges, such as occur when an improperly grounded person comes in physical contact the equipment. The electrostatic discharge that can result is capable of introducing errors and faults in such digital equipment.

In order to insure that such equipment is free from excess sensitivity to electrostatic effects, the equipment is tested prior to shipment. In these tests, the equipment is stressed as much as possible using conventional electrostatic discharge devices. These devices, which are typically controllable with respect to voltage, discharge rate and test duration nonetheless operate in wholly deterministic ways.

The main problem associated with deterministic electrostatic testing arises out of the fact that the machine under test is executing a stored test program which includes a plurality of individual diagnostic steps. In the ideal case, it is desirable to "zap" the machine during execution of each one of these steps to insure that induced hardware errors are handled correctly. To this end the diagnostic program steps include error trapping mechanisms in each of the steps to indicate the presence of a particular hardware error. However, the discharge test device and the machine itself are not set in synchronization with one another since static discharges in the field are themselves random events. Furthermore, attempts at synchronization are difficult because of different lengths of test programs and because of the varying number and kinds of program steps with which they are involved.

Currently, electrostatic discharge equipment is used to inject noise into operating data processing devices, usually in conjunction with diagnostic test routines. During these tests it is important to assure maximal diagnostic coverage in a minimal time. Maximal coverage means that a discharge occurs during each diagnostic step. However, because of the situation described above, many hours can be wasted both in computer time and in manpower if a well formulated test termination criterion is not implemented. In fact, without the introduction of randomness and multiplicity in testing, as proposed herein, it may not even be possible to insure total test program coverage.

In order to further clarify the test situation being considered herein, it can be assumed that a diagnostic test program which is repetitive in nature is running on a piece of data processing equipment under test. The test program particularly exercises the system error trapping mechanisms. The total length of run time which includes a number of iterations of the test program is referred to herein as the "experiment". In an asynchronous manner, an electrostatic discharge device produces electrostatic discharges into the system in which the sequence of instructions is executing. It is a test object to insure, with a certain level of confidence, that each portion of the repeating instruction sequence is executed simultaneously with an electrostatic discharge, at least once, in a minimal amount of time.

Such tests are required for a number of reasons. There is a significant need to test computer equipment prior to shipment for susceptibility to noise since the environments in which these machines are placed are subjected to a number of different noise sources. In particular, large scale computer installations often contain many computers together with associated input and output equipment. There are numerous non-ideal environmental situations which reside in customer installations that greatly affect the high availability of large systems. Some of these situations are customer power buses that serve as a common bus not only to one or more computers but also to other equipment as well. These buses generate noise which can enter computer systems. Additionally, miles and miles of under-the-floor cabling, oftentimes in neat long rows carry undesired cross talk noise to computer circuits. Telephone lines and teleprocessing equipment cables can also couple noise into computer systems. The equipment which is often used by customers to guarantee uninterrupted power, as well as other motors, generators and diesel engines used in operating environments, also generate a high frequency noise spectrum.

In general, noise may be radiated or conducted into a computer system. System operation in itself generates noise which can affect both the generating system and power or utility lines to which they are coupled. Indeed, the very grounding of systems can in fact have an effect on computer performance. It is thus seen that susceptibility to noise is a significant factor in the reliability, availability and serviceability of computer equipment. Accordingly, the desire for appropriate electrostatic testing is very important. Furthermore, one would like to be able to perform these tests in a minimal amount of time without sacrificing test thoroughness. This is becoming more difficult however because of the increased complexity of the systems and because of the length of the diagnostic test programs which are employed during the test phase.

The increasing complexity of such systems tends to decrease the efficiency of current electrostatic discharge testing equipment through longer testing times. Moreover, most electrostatic discharge testing systems are designed to test specific types of machines with specific characteristics (i.e. voltage operating level, system operation speed, etc). Such rigidly designed testing systems encounter difficulties when they are required to test machines which employ a range of operating voltages or system operation speeds. Often times expensive hardware changes must be performed, which in effect, pervert the test system from its original design.

Applicants are inventors of U.S. Pat. No. 4,961,157 which provides a method and apparatus for electrostatic discharge testing of machines. While U.S. Pat. No. 4,961,157 provided an important method and apparatus for performing electrostatic discharge testing, the applicants have sought to cure the mentioned disadvantages and problems of such testing through the system and method disclosed herein.

SUMMARY OF THE INVENTION

According to the present invention, a system and method are provided for performing electrostatic discharge testing of an electronic machine or machines which repetitively execute a stored program. The system comprises a computer, an electrostatic discharge interface unit, and a high voltage probe unit, all in circuit communication with each other. The computer includes test control logic capable of generating multiple, random, asynchronous control signals, a user interface, and at least one output port from which the control signals are accessible. The electrostatic discharge interface unit is responsive to the control signals generated from the computer. The high voltage probe unit is responsive to the electrostatic discharge interface unit and produces electrostatic discharges which are imparted on to a machine under test. The test control logic further comprises an interactive input graph and set utility which allow a user to specify the desire testing parameters.

The present invention also encompasses a method for performing electrostatic discharge testing of a machine by electrostatically exciting the machine under test in a random, asynchronous order by changing the states of a plurality of output lines from a first state to a second state. The first state existing for a specified time interval and the second state existing for a time interval determined randomly between a specified user maximum and minimum time interval.

The present invention preferably provides an interactive environment in which a user (that is, an electrostatic discharge test technician) is able to interactively specify either a test duration or a probability that at least one electrostatic discharge occurs during each program step of a repeating diagnostic routine. The user is also able to specify a proportion of program steps that are to be "hit". The interactive environment is implemented through the input graph and set utility.

Accordingly, when the user specifies a desired probability (confidence level), the user is also provided with an indication of the number of test iterations (the test duration) that will be required before a desired confidence level is reached. Furthermore, if the user specifies a test duration, say in seconds, then the apparatus of the present invention preferably provides an indication of the probability of successful discharge coverage for the specified test duration. Additionally, the user may provide an indicated proportion of the number of program steps to be covered by the discharge test.

Accordingly, it is an advantage of the present invention provide a system for reducing test durations associated with electrostatically stressing digital computer systems.

It is also an advantage of the present invention to provide a system for increasing the coverage of individual program steps with respect to the simultaneous or near simultaneous occurrence of disruptive electrostatic test discharges.

It is also an advantage of the present invention to provide improved testing of digital computer systems with respect to disruptive electrostatic discharge excitation.

It is also an advantage of the present invention to provide a system for electrostatic discharge testing of machines with multiple, random, asynchronous electrostatic discharges.

These and other advantages of the present invention will become more apparent from a detailed description of the invention.

BRIEF DESCRIPTION OF THE DRAWINGS

In the accompanying drawings, which are incorporated in and constitute a part of this specification, embodiments of the invention are illustrated, which, together with a general description of the invention given above, and the detailed description given below serve to example the principles of this invention.

DETAILED DESCRIPTION OF THE PREFERRED EMBODIMENT

Figure 1:
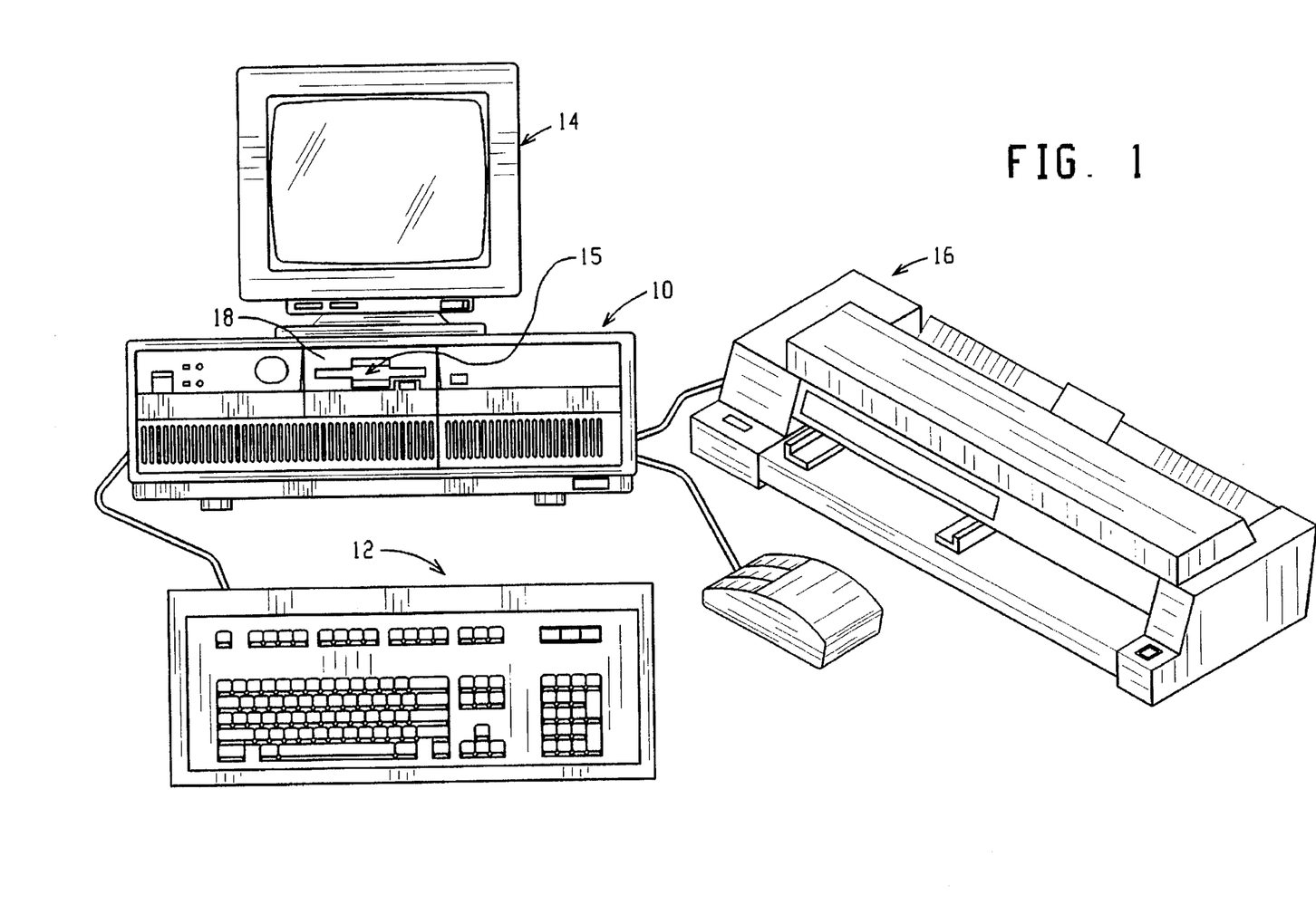
FIG. 1 is a perspective view of a personal computer incorporating the test control logic of the present invention.

Referring now to the drawings, and for the present to FIG. 1, a microcomputer embodying the test control logic of the present invention is shown and generally indicated at 10. The computer 10 may have an associated monitor 14, keyboard 12 and printer or plotter 16.

Figure 2:
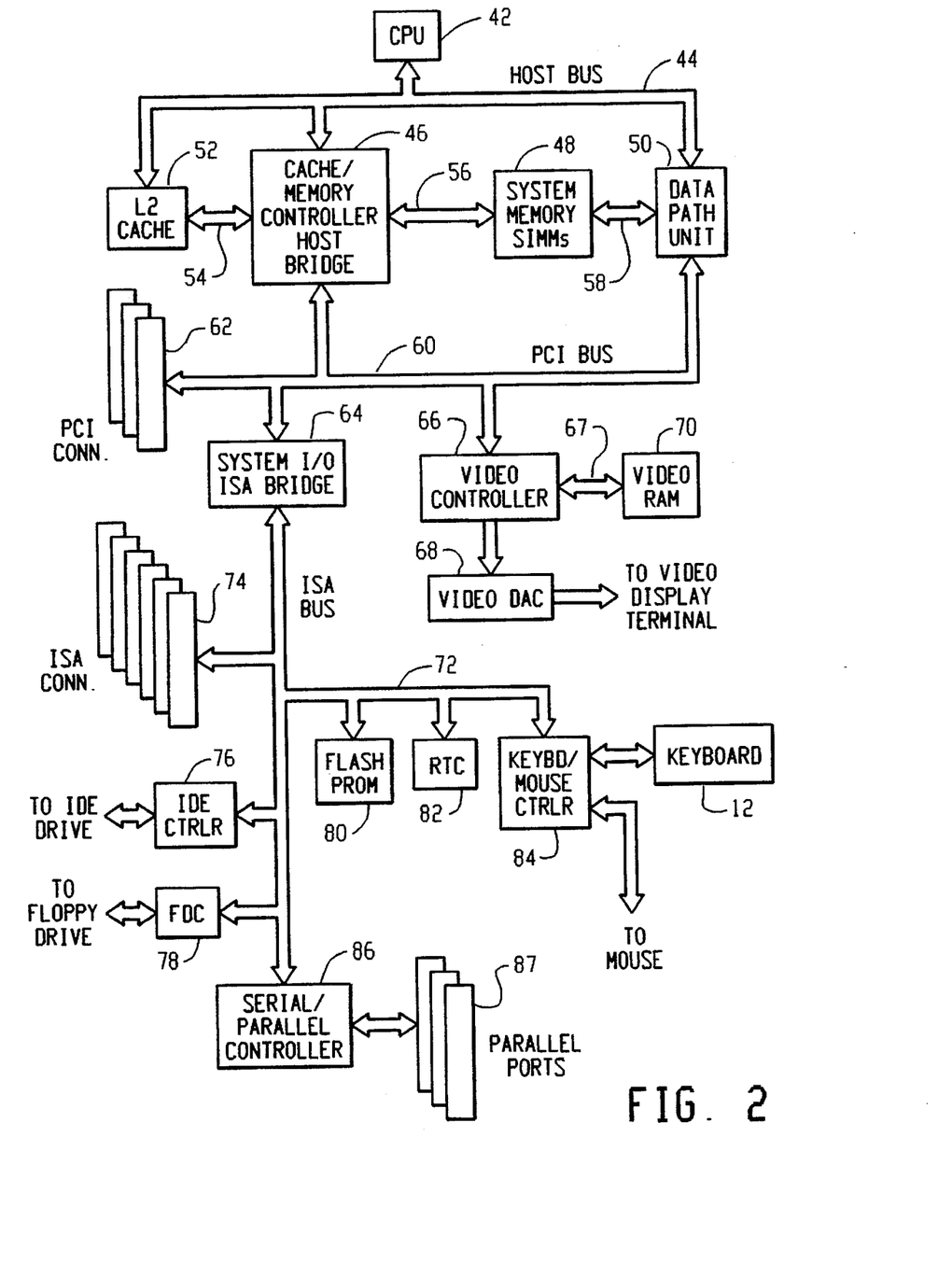
FIG. 2 is a schematic of view of certain components of the computer of FIG. 1.

Prior to relating the above structure to the present invention, a summary of the general operation of the personal computer system 10 merits review. Referring to FIG. 2, there is shown a block diagram of a personal computer system illustrating the various components of the computer system 10 in accordance with the present invention, including components mounted on a planar (not shown) and the connection of the planar to the I/O slots and other hardware of the personal computer system. Connected to the planar board (not shown) is the system processor 42. While any appropriate microprocessor can be Used as the CPU 42, one suitable microprocessor is the Pentium which is sold by Intel Corp. The CPU 42 is connected by a high speed CPU host bus 44 to a cache/memory controller and host bridge 46, data path unit 50, and second level cache memory (L2 cache) 52.

The cache/memory controller and host bridge 46 is connected to L2 cache 52 via a bus 54 and to a system memory 48 via a bus 56. The cache/memory controller and host bridge 46 integrates the L2 cache 52 and system memory 48 control functions and provides address paths and bus controls for transfers between the Host (CPU 42), system memory 48, and a Peripheral Component Interconnect (PCI) bus 60. The PCI bus 60 employs a 32 bit data bus that supports multiple peripheral components and add-in cards at a peak bandwidth of 132 MB/second.

During bus operations between the Host (CPU 42), system memory 48, and PCI bus 60, the cache/memory controller 46 provides the address paths and bus controls. The cache/memory controller 46 also controls data flow through the data path unit 50.

The data path unit 50 provides data path connections between the Host (CPU 42), system memory 48, and PCI bus 60. The system memory 48 is interfaced to the data path unit 50 via a data bus 58 whereby data is transmitted into and out of the system memory 48. The cache/memory controller 46 and the data path unit 50 provide a full function data path connection to system memory 48 and from PCI bus 60 to a Host subsystem (CPU 42).

PCI bus 60 is further connected to a plurality of PCI bus expansion slots 62 (three slots are shown), system I/O bridge controller 64, and video controller 66. The system I/O bridge controller 64 provides a bridge between the PCI bus 60 and an ISA bus 72 (or an EISA bus; not shown) and integrates many of the common I/O functions found in todays ISA (or EISA) based PC systems. The video controller 66, which is associated with a video RAM 70 for storing graphic information via a bus 67, is interfaced to the PCI Bus 60 to allow large amounts of data required for high performance graphics to be transmitted quickly to the video controller 66. Video signals generated by video controller 66 may be passed through a Digital to Analog Converter (DAC) 68 to a video display terminal or other display device.

Various peripheral devices are typically connected to the ISA bus 73, such as ISA expansion slots 74 (6 are shown), IDE hard disk controller 76, floppy disk controller (FDC) 78, flash PROM (BIOS) 80, real time clock 82, keyboard/mouse controller 84, serial/parallel controller 86, and optionally, Audio controller 88. The serial/parallel controller 86 is connected to serial communication ports (not shown) and parallel communication ports 87 (3 are shown) which allow the computer to communicate with various input/output devices, such as printer 16 (shown in FIG. 1) for example.

While the above description has been described with some particularity, it is to be understood that the present invention may be used in conjunction with other hardware configurations. For example, other peripheral components such an Ethernet controller, multimedia controller, or Small Computer System Interface II (SCSI II) controller may be added to PCI bus 60. Also the number of parallel ports 87 may be more or less than the three indicated.

Figure 3:
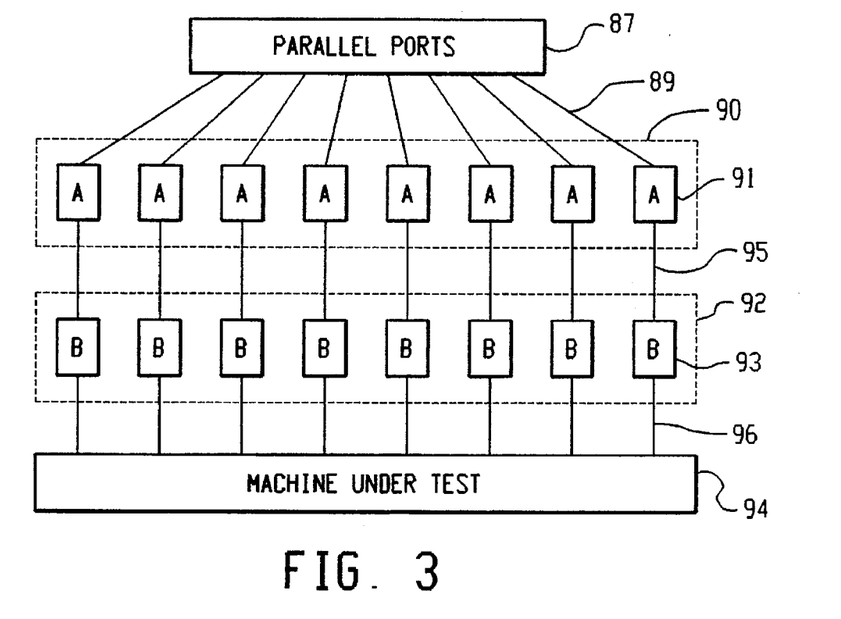
FIG. 3 is a block diagram showing the general interconnections between a parallel input/output port of the computer of FIG. 1, a machine under test, and various other components of the present invention.

Referring now to FIG. 3, a block diagram showing the general interconnections of various components of the illustrated embodiment is presented. Shown is a parallel input/output port 87 of the computer 10 of FIG. 1, an electrostatic discharge interface unit 90, a high voltage probe unit 92 and a machine under test 94. The parallel port 87 is in circuit communication with the electrostatic discharge interface unit 90 [hereinafter ESD unit] and linked to ESD unit 90 via a plurality of electrical conductors, such as conductor 89. The ESD unit 90 is in circuit communication with high voltage probe unit 92 [hereinafter HVP unit] and linked to HVP unit 92 through a second plurality of electrical conductors, such as conductor 95. The HVP 94 unit 92 is in circuit communication with machine 94 through a third plurality of conductors, such as conductor 96.

The ESD unit 90 comprises a plurality of individual electrostatic discharge control modules [hereinafter ESD control modules], such as 91 (also identified by reference letter "A"; a total of eight are shown in FIG. 3). The ESD control modules are primarily responsible for translating low power output signals from parallel port 87 to a high power control signals sufficient enough to drive the HVP unit 92. The HVP unit 92 is comprised of a plurality of individual high voltage probe modules [hereinafter HVP modules], such as 93 (Also identified by reference letter "B"; a total of eight are shown in FIG. 3). The HVP module includes a high voltage power supply, a probe relay, and a probe in contact with the machine under test 94.

Generally, low power control signals from parallel input/output port 87 are fed into ESD unit 90 (i.e. individual ESD control modules "A") wherein the low power control signals are translated to a high enough power level so that HVP unit 92 (i.e. individual HVP modules "B") can be driven. When an individual HVP module "B" receives a high power control signal from an individual ESD control module "A", the HVP module "B" generates an electrostatic discharge to the machine under test 94. The ESD control module "A" serves to both isolate the parallel port 87 from the other test equipment (HVP module 93, machine under test 84, power supplies, etc.) and to boost the power level of the control signals from the parallel port 87.

The system illustrated in FIG. 3 is also applicable to a plurality of machines under test. In such an embodiment, each HVP module "B" would be communication with a separate and distinct machine under test. Thus, the number of machines under test may be as many as the number of HVP modules "B" available in the current testing system. The need for such an embodiment may arise when large numbers of machines are required to be tested, such as in high volume manufacturing environments.

Figure 4:
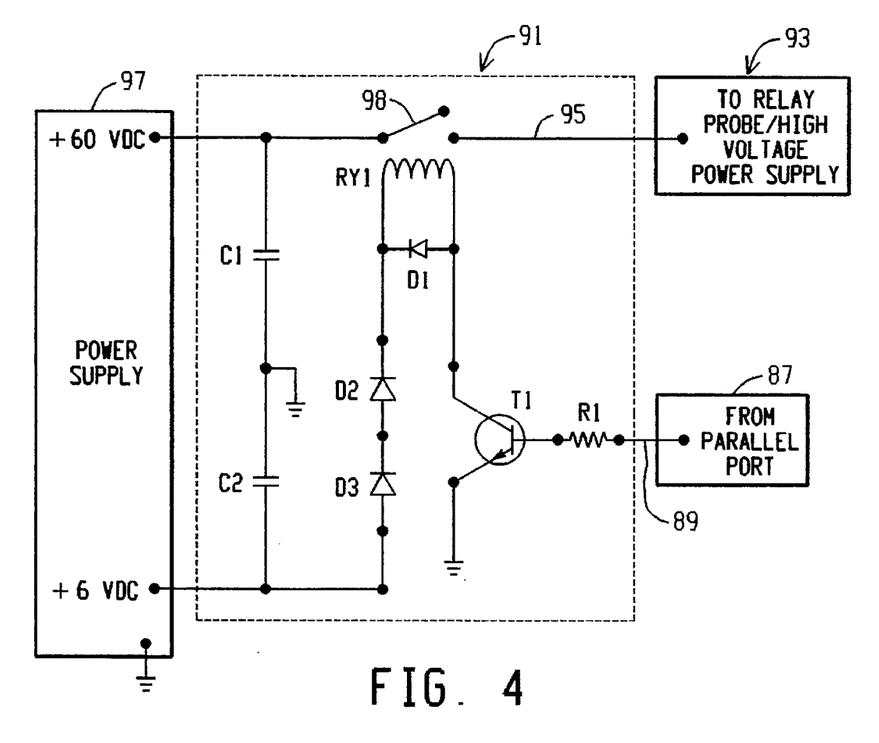
FIG. 4 is schematic diagram of an electrostatic discharge control module of the present invention.

Referring now to FIG. 4, a schematic diagram of ESD control module 91 (and therefore all ESD control modules "A") of the present invention is shown. The ESD control module 91 includes capacitors C1 and C2, diodes D1, D2, and D3, transistor T1, relay RY1, and resistor R1, all connected to each other as shown in FIG. 4.

Parallel port 87 is connected to the base of transistor T1 through current limiting resistor R1. Power supply 97 is connected to the collector of transistor T1 through diodes D2 and D3 and relay RY1. Capacitors C1 and C2 are provided to filter AC signals from the power supply 97 D.C. output signals (i.e. +60 VDC and +6 VDC). The emitter of transistor T1 is connected to ground. Transistor T1 acts as an "open circuit" when there is no current flowing through resistor R1 into the base of T1. This "open circuit" prevents current from flowing through relay RY1 and thus leaves relay RY1 unenergized and its contact 98 in the normally open position.

When a control signal (typically 0 to 5 volts) from parallel port 87 is applied to conductor 89, a small current flows into the base of transistor T1 through resistor R1. The small current causes the transistor T1 to conduct current from its collector to its emitter. In this manner, the transistor T1 forms a "closed" or "short" circuit between its collector terminal and emitter terminal and thus allows current to flow between the two terminals. The transistor T1 and resistor R1, thus, form a switching circuit by T1 acting as an "open circuit" when there is no current flowing into its base terminal, and acting as a "closed circuit" when there is current flowing into the base terminal.

When transistor T1 forms a "closed circuit", the power supply 97 provides a voltage of nominally +5 VDC (due to small voltage losses caused by diodes D2 and D3) to relay RY1. Relay RY1 is thereby energized and normally open contact 98 closes. When normally open contact 98 closes, the power supply 97 provides +60 VDC signal to the HVP module 93. The HVP module 93 then produces an electrostatic discharge to the machine under test. The +60 VDC signal is used to energize a relay in the HVP module 93 which closes a contact thereby causing an electrostatic charge to be discharged through a probe in contact with the machine under test 94. In the illustrated embodiment, C1 and C2 are 0.1 microfarad capacitors, D1, D2, and D3 are silicon switching diodes (e.g. 1N914 or 1N4148), T1 is an NPN-type switching transistor, R1 is a 1000 ohm resistor, and RY1 is a 5 volt DC relay with a coil resistance of 250 ohms and with SPST normally open contacts.

Figure 5A:
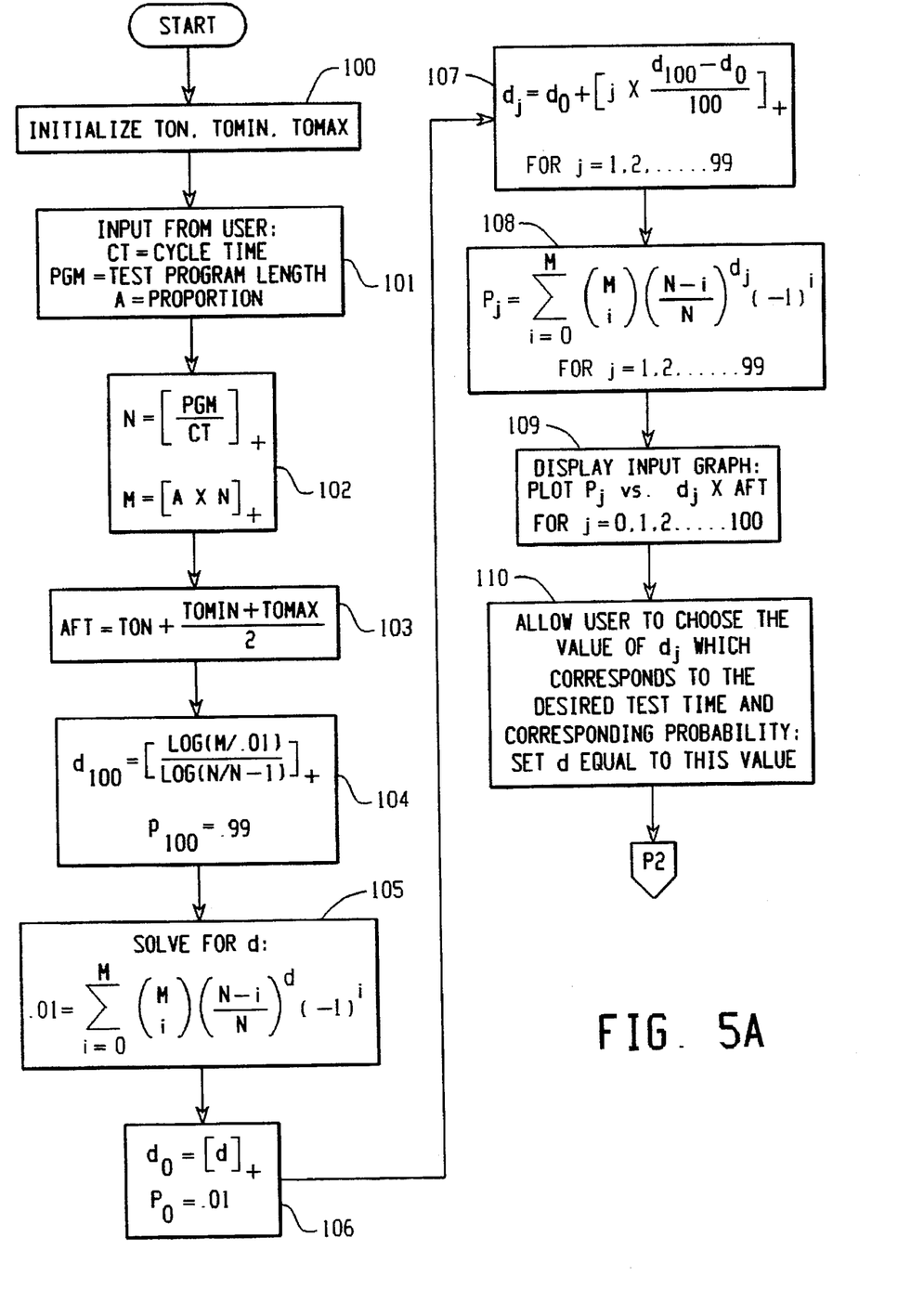
FIGS. 5A and 5B are flowcharts illustrating the test control logic for generating multiple, random, asynchronous control signals.
Figure 5B:
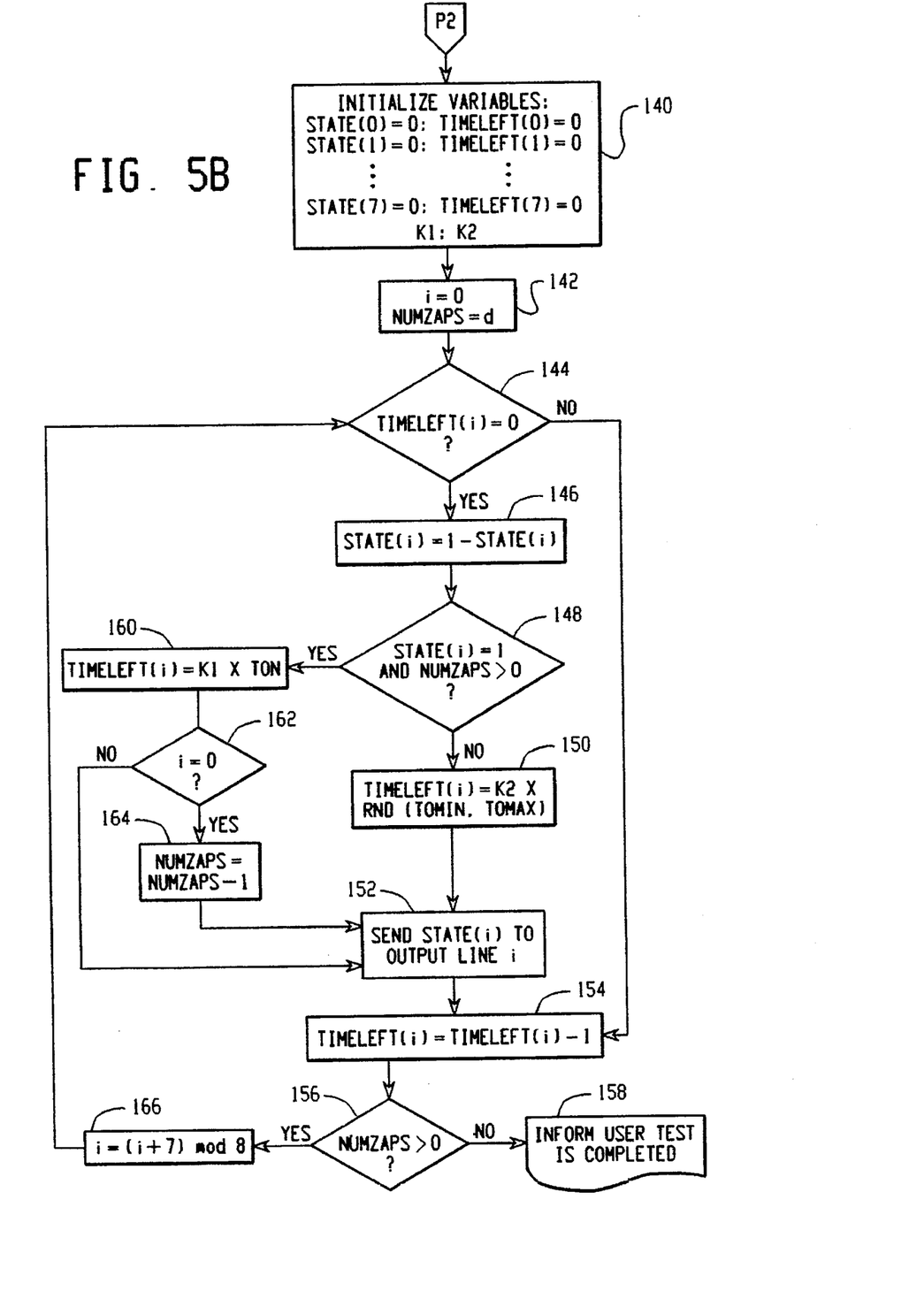

FIGS. 5A and 5B show flowcharts illustrating test control logic for generating multiple, random, asynchronous control signals from parallel port 87 to HVP module 92. In particular, as indicated in the flowchart in FIG. 5A, the test control logic requests the user to supply parameters, namely the cycle time, CT, the length, PGM, of the repetitive test program executing in machine 94 (shown in FIG. 3), and the desired proportion, A, of the program to be covered. Two of these parameters may be specified in units of seconds. The third is preferably specified as a decimal number from 0.0 to 1.0 and indicates the proportion of program steps to be covered.

The parameters, CT and PGM, are used to determine the number of steps N in the diagnostic program running on the machine under test. Thus, it is seen that cycle time CT represents the execution time of the individual steps or subprocedures in the diagnostic program. It is an object of the present invention to insure with a specified level of confidence that a discharge from HVP module 92 (shown in FIG. 3) is provided to machine 94 during the execution of M of the N program steps. This is accomplished in a random, asynchronous fashion with multiple discharges from HVP module 92. Nevertheless, the randomness is controlled in terms of duration and firing time.

In the event that M=N (as for example when A=1.0), each program step is specified. However, when A is less than 1.0, fewer than all N steps are targeted. The choice of a value for A less than 1.0 is particularly useful when the diagnostic program includes a step which is a long initialization routine for which hardware testing is less critical or even unnecessary.

In operation, the user, in response to queries generated by the test control logic supplies cycle time, proportion and test program length information. The test control logic then employs this information along with the control signal's pre-stored waveform characteristics (namely, the "on" time, TON, maximum "off" time, TOMAX, and minimum "off" time, TOMIN) to generate an input graph from which the user may specify an experiment which is limited by a specific run-time or the achievement of a certain probability of producing a discharge during each of the steps in the diagnostic program (See FIG. 6). The input graph is calculated by pre-computing the probability of test coverage P and the test time in seconds. The illustrated embodiment employs an iterative approach to solving the required values of $d_0$ to $d_{100}$ and $P_0$ to $P_{100}$ which are used to generate the input graph.

The iterative approach for computing the required valued of $d_0$ to $d_{100}$ is characterized by Eqn.'s 1–4. The value of $d_{100}$ is determined by Eq. 1 as follows:

$$d_{100} = \left[ \frac{\log(M/.01)}{\log(N/N-1)} \right]_+ \quad \text{(Eq. 1)}$$

In Eq. (1) above, the logarithm specified can be to any base, but for ease of computation it is preferable to use the natural logarithm, that is the logarithm to the base e.

The value of $d_0$ is determined by first solving Eq. 2 for d, and then second by equating $d_0$ to the smallest integer value greater than d in Eq. 3:

$$.01 = \sum_{i=0}^{M} \binom{M}{i} \left( \frac{N-i}{N} \right)^d (-1)^i \quad \text{(Eq. 2)}$$

$$d_0 = [d]_+ \quad \text{(Eq. 3)}$$

The values for $d_1$ through $d_{99}$ are computed through Eq. 4:

$$d_j = d_0 + \left[ j* \frac{d_{100} - d_0}{100} \right]_+ \quad \text{(Eq. 4)}$$

where j=1,2, ... 99.

The probabilities $P_0$ to $P_{100}$ are also determined by an interactive process through Eqn.'s 5–7. The value of $P_{100}$ is set by Eq. 5 to 0.99:

$$P_{100} = 0.99 \quad \text{(Eq. 5)}$$

The value of $P_0$ is set to 0.01 by Eq. 6:

$$P_0 = 0.01 \quad \text{(Eq. 6)}$$

The values of $P_1$ through $P_{99}$ are computed through Eq. 7:

$$P_j = \sum_{i=0}^{N} \binom{M}{i} \left( \frac{N-i}{N} \right)^{d_j} (-1)^i \quad \text{(Eq. 7)}$$

where j=1, 2, ... 99.

Once the values of $P_0$ to $P_{100}$ and $d_0$ to $d_{100}$ have been computed, the test control logic generates a plot of $P_j$ versus $d_j$ * AFT, for j=0, 1, 2, ... 100. The values are plotted on cartesian coordinate system and the resulting graph is displayed on the monitor where the user may interactively select a desired probability of test coverage or a run-time (See FIG. 6).

Attention is now specifically directed to the flowcharts illustrated in FIGS. 5A and 5B. In step, 100, the control signal waveform characteristics, namely, "on" time, TON, maximum "off" time, TOMAX, and minimum "off" time, TOMIN, are initialized to preset values stored in the test controller logic. It should, however, be mentioned that in an alternative embodiment the user is given an option which allows the entry of user-defined control waveform characteristics or preset waveform characteristics. The test control logic then requests input information from the user in step 101. In particular, in FIG. 5A, the user is prompted to supply cycle time, CT, test program length, PGM, and proportion, A. Next, the test control logic computes a value for N in step 102 by dividing PGM by CT and rounding up to the next integer value. In particular, in steps 102, 104, 106, and 107 (discussed below) the square brackets having a subscripted "+" sign denote "the smallest integer greater than." A value for M is also computed in step 102 as [A×N], where A is the user specified proportion.

Next, the test control logic computes an average firing time interval duration, AFT, as TON+(TOMIN TOMAX)/2 in step 103 as shown. Next, in step 104 the test control logic determines the value of $d_{100}$ via Eq. 1 and the value of $P_{100}$ is set to 0.99 via Eq. 5. In step 105, the test control logic computes the value of d through Eq.2.

One the value of d is computed, the value of $d_0$ is set equal to the smallest integer larger than d in step 106. The test control logic next, in step 107, computes the values of $d_1$ through $d_{99}$ via Eq. 4. At this point, the values $d_0$ through $d_{100}$ have all been computed by the test control logic. The test control logic next computes the values of $P_1$ through $P_{99}$ in step 108 through Eq. 7.

In step 109, the test control logic generates the input graph by plotting $P_j$ vs. $d_j$ * AFT, for j=0, 1, 2, ... 100, on a cartesian coordinate system. The resulting graph (FIG. 6) is then displayed on the computer monitor. In step 110, the user interactively selects either a desired probability of test coverage or a desired test run-time through the information provided by the input graph. This is accomplished by allowing the user to position a curser along the points of the input graph which correspond the probability of test coverage and the associated test run-time. If a probability of test coverage is selected $P_j$, the number of discharges, d, is set equal to $d_j$ and the corresponding test run-time ($d_j$ * AFT) is displayed. Alternatively, if a specific test run-time ($d_j$ * AFT) is selected, then number of discharges, d, is set equal to $d_j$ and the probability of test coverage $P_j$ is displayed. The user may now begin the test or exit and start the procedure over again.

It is thus seen that the test control logic, in response to user input parameters A, CT and PGM and a choice of termination procedure, determines a value for d, a measure of test duration. In the event that the user specifies a probability P, the test control logic displays the corresponding test time in seconds. In the converse situation in which an experiment test time is supplied by the user, the test control logic displays to the user the probability of test coverage P (See FIG. 6).

Once the user has entered the desired test information, control is passed to the multiple, asynchronous, random fire timing logic [hereinafter MARFT logic] within the test control logic. This function is implementable as indicated in the flow chart in FIG. 5B.

The MARFT logic changes the states of each output line from parallel port 87 (in FIG. 3) in an asynchronous, random manner. After initialization of variables, each output line is fired for a time interval equal to TON. The MARFT logic maintains each output line in the fired, or "on", state until the time period equivalent to (K1 * TON) expires. Each time an output line is placed in the "on" state, a counter subtracts a value of one from the number of required discharges or zaps. Thereafter, the MARFT logic generates an "off" time for each output line. The "off" time is determined as a random value between a specified minimum "off" time, TOMIN, and a specified maximum "off" time, TOMAX times a constant K2. Each output line is then maintained in its "off" state for its specifically generated random "off" time. Since each output line is in circuit communication with an ESD control module "A" (in FIG. 3), which is further in circuit communication with an HVP module "B" (in FIG. 3), electrostatic discharges are delivered to the machine under test in accord with the state of the output lines (reference numeral 89 and the like shown FIG. 3). In this manner, multiple, asynchronous, random electrostatic discharges are produced.

More particularly, variables STATE(0) through STATE(7) are initialized to a value of zero in step 140. STATE(0) through STATE(7) represent the states of output lines, such as conductor 89 (FIG. 3), and have values of either "1" or "0". In the illustrated embodiment, a value of "0" indicates that the output line is in a LOW state (i.e. not currently firing). Conversely, a value of "1" indicates that the output line is in a HI state (i.e. currently firing). Note that the STATE variables may extend to STATE(n), where n is equal to the number of output lines that the system has available.

Also in step 140, constants K1 and K2 are initialized. The constants K1 and K2 are initialized to values based on the computer speed, or cycle time, on which the test control logic is executing. The constants K1 and K2 are set so that the variable TIMELEFT(i), in steps 160 and 160, when multiplied by K1 or K2, can be used to count down the amount of time remaining. Thus, the values to which K1 and K2 are initialized will depend on the characteristics of the computer on which the test control logic is executing.

Also in step 140, variables TIMELEFT(0) through TIMELEFT(7) are initialized to a value of zero. The TIMELEFT variables are utilized by the MARFT logic as timers for timing how long each output line (STATE(0) through STATE(7)) will be in a given HI ("1"; firing) or LOW ("0"; not firing) state.

In step 142, a variable "i" is initialized to a value of zero and NUMZAPS is initialized to equal the duration "d", which is in units of 'zaps'. The variable "i", which represents a particular output line, is used in a modulo counter in step 166. The modulo counter in step 166 sequentially cycles the "i" variable from a value of zero to seven at increments of one. Note, that just with the variables in step 140, the modulo counter may set up to sequentially cycle to a value "n", where "n" is the number of available output lines minus 1.

After the variables have been initialized (steps 140–142), the TIMELEFT(0) variable (signifying the first output line since "i" equals zero initially) is examined, in step 144, to determine if a change of state of the first output line is required. If TIMELEFT(0) equals zero, then the STATE(0) is changed to 1-STATE(0) (i.e. from "0" to "1").

Step 148 examines the state variable of the current output line and the number of required discharges to determine if the state variable of the current output line has been changed to a HI state (i.e. STATE(0)=1) and the number of required discharges is still greater than zero (NUMZAPS>0). If this condition is affirmative, then the TIMELEFT(0) is set equal to K1 * TON in step 160.

In step 162, the MARFT logic determines if the modulo counter of step 166 has cycled back to the first output line. If this condition is affirmative, then the number of required discharges is reduced by a value of one (NUMZAPS=NUMZAPS−1) and the state of the current output line (STATE(0)=1) is sent, in step 152, to the parallel port 87 (shown in FIG. 3). Otherwise, the state of the current output line is sent to the parallel port 87 (shown in FIG. 3) without subtracting the number of required discharges. Step 152 causes the parallel port 87 (shown in FIG. 3) to physically change the states (i.e. from LOW to HI) of its output lines and thereby causes HVP module "B" (in FIG. 3) to impart an electrostatic discharge to the machine under test.

After the state of the output line is sent to the parallel port 87, TIMELEFT(0) (which is currently equal to TON) is decremented by a value of one in step 154. Step 156 examines the NUMZAPS variable to determine if the number of required zaps is still greater than zero. If the condition is affirmative, then the "i" variable is incremented to a value of "1" by the modulo counter of step 166.

Similarly, for when "i" equals one, the second output line changes state from LOW to HI. All output lines (zero through seven) are eventually placed in the HI state for a time period equal to K1 * TON.

Once all of the output lines have been placed in the HI state and the "on" time has expired, TIMELEFT(0) will equal zero in step 144. Step 146 will set the STATE variable for the first output line to LOW (i.e. STATE(0)=0). Since the state variable has not been changed to "1", but instead to "0" (i.e STATE(0)=0), the MARFT logic determines an "off" period for the first output line. The "off" period is determined, in step 150, by setting TIMELEFT(0) equal to a randomly generated value between the values of TOMIN (minimum "off" time) and TOMAX (maximum "off" time) multiplied by constant K2. Once the "off" time has been determined, the state of the output line is sent, in step 152, to the parallel port 87.

Step 154 decrements TIMELEFT(0) (currently the "off" time) by a value of one and step 156 examines the NUMZAPS variable to determine if the number of required zaps is still greater than zero. If condition is affirmative, then the "i" variable is set to a value of "1" by the modulo counter and the "off" procedure repeats for the second output line.

Similarly, for when "i" equals one, the second output line changes state from HI to LOW. As the modulo counter of step 166 cycles the "i" variable, all output lines (zero through seven) are eventually placed in the LOW state for a randomly generated "off" period. Because each "period" is randomly generated for each output line, each "off" period will expire at different time. The result is that each output line hereinafter will fire asynchronous from the other output lines. The procedure will continue to repeat until the NUMZAPS variable in step 156 equals zero. When NUMZAPS equals zero, the number of required discharges has been performed and the user is informed in step 158 that the test is completed.

Figure 6:
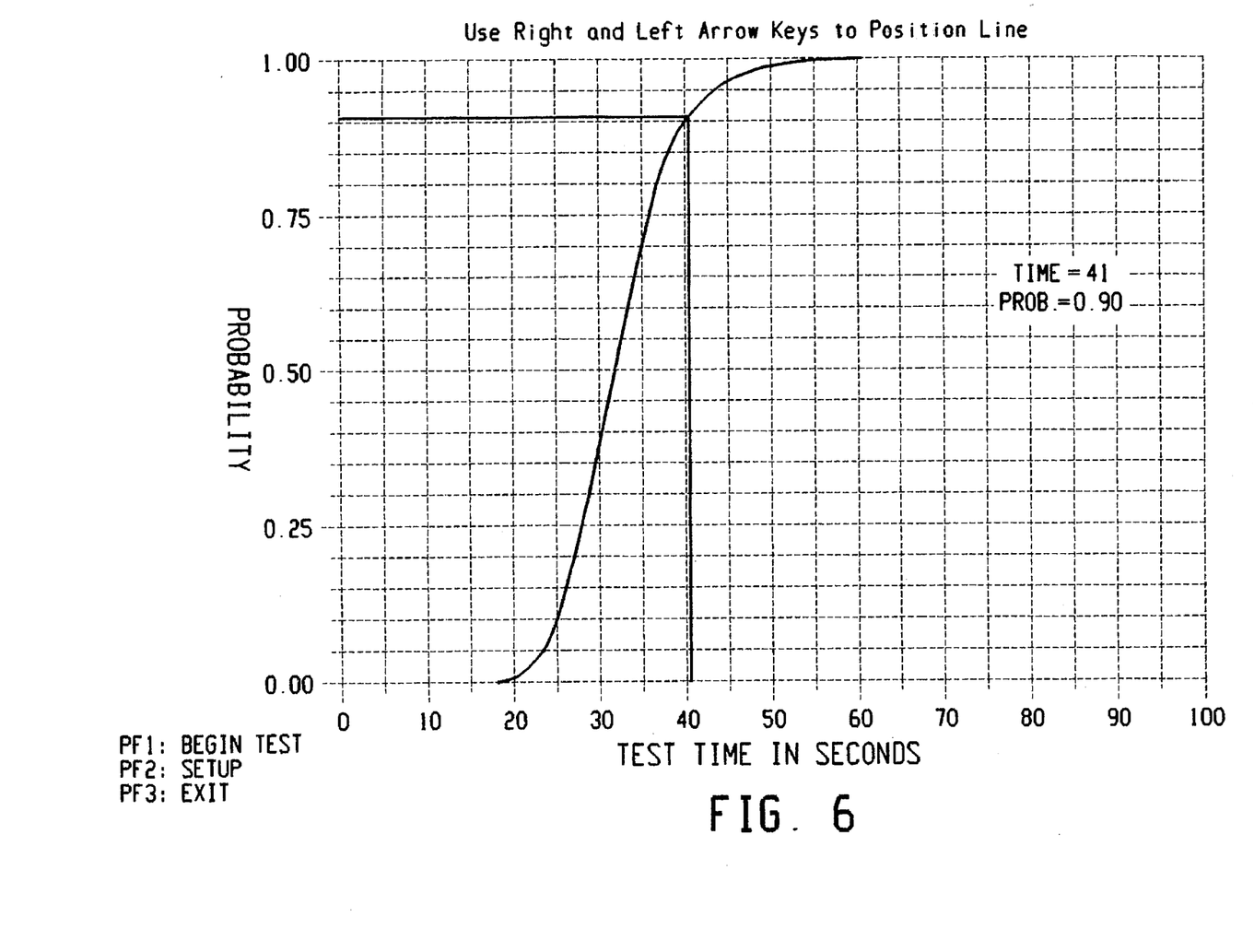
FIG. 6 is a illustration of the interactive input graph generated by the test control logic.

Referring now to FIG. 6, an interactive input graph of the present invention is shown. The interactive input graph is generated by the test control logic and allows the user to control and enter the parameters of the test to be performed. Additionally, a setup utility is provided in which a user may change or modify pre-stored testing parameters such as the control signal's waveform characteristics (i.e. "on" time, maximum "off" time, minimum "off" time, etc). Through the modification of such parameters, the testing environment may be changed from a system which generates multiple, asynchronous, random firing electrostatic discharges to a system which generates multiple, synchronous firing electrostatic discharges. Such a change may be accomplished by modifying the control signal's waveform characteristics so that the maximum "off" time and the minimum "off" time are equal to each other. In this manner, each control signal waveform will fired on and turned off synchronously.

While the present invention has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. For example, number of parallel ports, or the number of output lines may be increase. Therefore, the invention in its broader aspects is not limited to the specific details, representative apparatus and method, and illustrative examples shown and described. Accordingly, departures may be made from such details without departing from the spirit or scope of the applicant's general inventive concept.

What is claimed is:

1. A system for performing electrostatic discharge testing of a machine comprising:
   (a) a computer having:
      (1) test control logic for generating multiple, random, asynchronous control signals on a plurality of output lines,
      (2) a user interface, and
      (3) at least one output port for outputting said multiple, random, asynchronous control signals, said output port comprising said plurality of output lines,
   (b) an electrostatic discharge interface unit in circuit communication with said plurality of output lines and responsive to said multiple, random, asynchronous control signals;
   (c) a high voltage probe unit in circuit communication with said electrostatic discharge interface unit and the machine to be tested and responsive to said electrostatic discharge interface unit.

2. The system of claim 1 wherein said electrostatic discharge interface unit comprises at least one electrostatic discharge control module.

3. The system of claim 2 wherein said electrostatic discharge interface unit comprises a plurality of electrostatic discharge control modules.

4. The system of claim 2 wherein said electrostatic discharge control module comprises:
   (a) a control relay, and
   (b) a switching circuit in circuit communication with said control relay.

5. The system of claim 4 further comprising a DC power supply in circuit communication with said electrostatic discharge control module.

6. The system of claim 1 the user interface comprises an interactive input graph.

7. The system of claim 6 wherein said interactive input graph comprises a plot of probability of test coverage vs. test time.

8. The system of claim 1 wherein said test control logic comprises predetermined control signal waveform characteristic data.

9. The system of claim 1 wherein said test control logic comprises a setup utility for user entry of control signal waveform characteristic data.

10. The system of claim 1 wherein said test control logic comprises multiple, asynchronous, random fire timing logic.

11. The system of claim 10 wherein said multiple, asynchronous, random fire timing logic comprises:
    (a) a plurality of state variables;
    (b) a plurality of time variables;
    (c) decrementing logic for decrementing said plurality of time variables;
    (d) modulo counter logic for cycling through said plurality of state variables and said plurality of time variables; and
    (e) random number logic for generating random numbers to determine said plurality of time variables.

12. The system of claim 10 wherein said multiple, asynchronous, random fire timing logic further comprises switching logic for changing said asynchronous control signals from a first state to a second state.

13. A system for performing electrostatic discharge testing of a plurality of machines, comprising:
    (a) a computer having:
       (1) test control logic for generating multiple, random, asynchronous control signals on a plurality of output lines,
       (2) a user interface, and
       (3) at least one output port for outputting said multiple, random, asynchronous control signals, said output port comprising said plurality of output lines,
    (b) an electrostatic discharge interface unit in circuit communication with said plurality of output lines and responsive to said multiple, random, asynchronous control signals;
    (c) a high voltage probe unit in circuit communication with said electrostatic discharge interface unit and the plurality of machines to be tested and responsive to said electrostatic discharge interface unit.

14. The system of claim 13 wherein said electrostatic discharge interface unit comprises a plurality of electrostatic discharge control modules.

15. The system of claim 14 wherein each of said electrostatic discharge control modules comprises:
    (a) a control relay, and
    (b) a switching circuit in circuit communication with said control relay.

16. The system of claim 15 further comprising a DC power supply in circuit communication with each of said electrostatic discharge control modules.

17. The system of claim 13 wherein the user interface comprises an interactive input graph.

18. The system of claim 17 wherein said interactive input graph comprises a plot of probability of test coverage vs. test time.

19. The system of claim 13 wherein said test control logic comprises predetermined control signal waveform characteristic data.

20. The system of claim 13 wherein said test control logic comprises a setup utility for user entry of control signal waveform characteristic data.

21. The system of claim 13 wherein said test control logic comprises multiple, asynchronous, random fire timing logic.

22. The system of claim 21 wherein said multiple, asynchronous, random fire timing logic comprises:
   (a) a plurality of state variables;
   (b) a plurality of time variables;
   (c) decrementing logic for decrementing said plurality of time variables;
   (d) modulo counter logic for cycling through said plurality of state variables and said plurality of time variables; and
   (e) random number logic for generating random numbers to be stored in said plurality of time variables.

23. The system of claim 21 wherein said multiple, asynchronous, random fire timing logic further comprises switching logic for changing said asynchronous control signals from a first state to a second state.

24. A method of performing electrostatic discharge testing of a machine comprising the step of:
   electrostatically exciting said machine in a random, asynchronous order by changing the states of a plurality of electrostatic discharge output lines from a first state to a second state wherein said first state exists for a specified time interval and said second state exists for a time interval determined randomly between a specified maximum and minimum time interval.

25. The method of claim 24, further comprising the steps of:
   (a) storing user specified test parameters in a memory;
   (b) calculating a discharge total and a probability of test coverage value from said user specified parameters; and
   (c) displaying an input graph on a display, said graph comprising a plot of probability of test coverage versus test time.

26. The method of claim 25, further comprising the step of displaying a selected probability of test coverage and a corresponding test time.

27. The method of claim 24, further comprising the step of decrementing a counter when said electrostatic discharge output lines are in said first state.

* * * * *

UNITED STATES PATENT AND TRADEMARK OFFICE
CERTIFICATE OF CORRECTION

PATENT NO. : 5,661,657
DATED : August 26, 1997
INVENTOR(S) : Jordan, et al.

It is certified that error appears in the above-identified patent and that said Letters Patent is hereby corrected as shown below:

In column 11, line 66, following "claim 1" please insert -- wherein --.

Signed and Sealed this

Twenty-fifth Day of November, 1997

Attest:

BRUCE LEHMAN

Attesting Officer

Commissioner of Patents and Trademarks